(12) United States Patent
Utsugi et al.

(10) Patent No.: US 9,670,525 B2
(45) Date of Patent: Jun. 6, 2017

(54) METHOD FOR MEASURING CHOLESTEROL IN HIGH-DENSITY LIPOPROTEIN

(71) Applicant: KYOWA MEDEX CO., LTD., Chuo-ku, Tokyo (JP)

(72) Inventors: Rie Utsugi, Sunto-gun (JP); Yuki Katayama, Sunto-gun (JP)

(73) Assignee: KYOWA MEDEX CO., LTD., Tokyo (JP)

( * ) Notice: Subject to any disclaimer, the term of this patent is extended or adjusted under 35 U.S.C. 154(b) by 172 days.

(21) Appl. No.: 14/420,925

(22) PCT Filed: Aug. 30, 2013

(86) PCT No.: PCT/JP2013/073250
§ 371 (c)(1),
(2) Date: Feb. 11, 2015

(87) PCT Pub. No.: WO2014/034823
PCT Pub. Date: Mar. 6, 2014

(65) Prior Publication Data
US 2015/0232914 A1    Aug. 20, 2015

(30) Foreign Application Priority Data
Aug. 31, 2012  (JP) .................. 2012-191144

(51) Int. Cl.
*C12Q 1/60*   (2006.01)
(52) U.S. Cl.
CPC ......... *C12Q 1/60* (2013.01); *G01N 2333/904* (2013.01); *G01N 2333/918* (2013.01)
(58) Field of Classification Search
None
See application file for complete search history.

(56) References Cited

U.S. PATENT DOCUMENTS

| | | | |
|---|---|---|---|
| 3,956,069 A * | 5/1976 | Allain | C12Q 1/32 435/14 |
| 4,161,425 A * | 7/1979 | Perry | C12Q 1/60 435/11 |
| 4,851,335 A | 7/1989 | Kerscher et al. | |
| 4,892,815 A | 1/1990 | Kerscher et al. | |
| 5,384,248 A | 1/1995 | Sakata et al. | |
| 5,691,159 A | 11/1997 | Miyauchi et al. | |
| 7,811,780 B2 | 10/2010 | Katayama et al. | |
| 2009/0246807 A1 | 10/2009 | Sun | |
| 2009/0280514 A1 | 11/2009 | Katayama et al. | |

FOREIGN PATENT DOCUMENTS

| | | |
|---|---|---|
| EP | 0 753 583 | 1/1997 |
| EP | 1 555 326 | 7/2005 |
| JP | 62-69999 | 3/1987 |
| JP | 63-126498 | 5/1988 |
| JP | 3-10696 | 1/1991 |
| JP | 08-116996 | 5/1996 |
| JP | 08-131197 | 5/1996 |
| JP | 08-201393 | 8/1996 |
| JP | 09-299 | 1/1997 |
| JP | 09-285298 | 4/1997 |
| WO | 97/00971 | 1/1997 |
| WO | 97/40376 | 10/1997 |
| WO | 00/52480 | 9/2000 |
| WO | 2004/035816 | 4/2004 |
| WO | 2006/118199 | 9/2006 |

OTHER PUBLICATIONS

Defintion or reagent from http://chemistry.about.com/od/chemistryglossary/g/reagent-definatio.htm downloaded Sep. 28, 2016.*
Katayama et al., "Shinki HDL-C Sokuteiho no Shokai", Seibutsu Shiryo Bunseki, vol. 32, No. 1 (2009) 60 (with English translation).

* cited by examiner

*Primary Examiner* — Susan Hanley
(74) *Attorney, Agent, or Firm* — Fitzpatrick, Cella, Harper & Scinto

(57) ABSTRACT

Provided is a method for measuring cholesterol in high-density lipoprotein (HDL) simply and accurately. A method for measuring cholesterol in high-density lipoprotein in a specimen, comprising reacting the specimen with i) a cholesterol ester hydrolase and a cholesterol oxidase, or ii) a cholesterol ester hydrolase, an oxidized coenzyme, and a cholesterol dehydrogenase, in an aqueous medium comprising at least one substance selected from the group consisting of pyridinium salts and quaternary ammonium salts each having a specific structure, and a polyanion to form hydrogen peroxide or reduced coenzyme and measuring the formed hydrogen peroxide or reduced coenzyme.

28 Claims, No Drawings

METHOD FOR MEASURING CHOLESTEROL IN HIGH-DENSITY LIPOPROTEIN

This application is a National Phase of PCT/JP2013/073250 filed Aug. 30, 2013, which in turn claims benefit of Japanese Application No. 2012-191144 filed Aug. 31, 2012.

TECHNICAL FIELD

The present invention relates to a method, a reagent and a kit for measuring cholesterol in high-density lipoprotein in a specimen.

BACKGROUND ART

Lipoproteins in the living body are classified into high-density lipoprotein (hereinafter abbreviated as HDL), low-density lipoprotein (hereinafter abbreviated as LDL), very low-density lipoprotein (hereinafter abbreviated as VLDL), and chylomicron (hereinafter abbreviated as CM) according to their specific gravity. Each class of the lipoproteins has a considerably different function in vivo mainly depending on the type of the apoprotein and also has a different lipid composition. It is known that, of these lipoproteins, HDL is involved in the removal action of cholesterol accumulated in cells to receive cholesterol from tissues including arterial walls and is a risk prevention factor for various arterial scleroses, including coronary arteriosclerosis, and therefore, its level in blood is a useful index for predicting the onset of arteriosclerotic diseases.

The conventional methods for measuring cholesterol in HDL (hereinafter abbreviated as HDL cholesterol) consist of two steps: a fractionation operation by an ultracentrifugation method, an immunochemical method, an electrophoresis method, or a precipitation method, and cholesterol determination. However, the fractionation operations are complicated and time-consuming and also have a problem in terms of safety. Thus, these measurement methods involving the fractionation operations are extremely inefficient and are not suited for practical use.

Various measurement methods have been reported in recent years to solve the above problems. Known examples of the methods include: a method for the specific fractional determination of HDL cholesterol, which involves reacting serum or plasma with a cholesterol esterase and a cholesterol oxidase in a buffer solution comprising the above enzymes as well as a bile acid salt, a bile acid derivative, or dioctylsulfosuccinate (see patent document 1) and a method for measuring HDL cholesterol, which involves reacting serum with pancreas-derived cholesterol esterase and cholesterol oxidase in a buffer solution comprising the enzymes, a surfactant belonging to the group of bile acids, and a nonionic surfactant at a specific pH and a specific temperature (see patent document 2). In the method described in patent document 2, the reaction of LDL cholesterol with the enzymes proceeds first and HDL cholesterol can then be measured. However, these measurements require long time and have not always been measurement methods specific for HDL cholesterol.

Known examples of methods for measuring HDL cholesterol by aggregating lipoproteins other than HDL include: a method using a reagent for aggregating lipoproteins other than HDL, such as dextran sulfate, a divalent metal salt, and a chemically modified enzyme (see patent document 3); a measurement method using a reagent forming a complex with lipoproteins other than HDL, such as a polyanion, and a surfactant not dissolving lipoproteins, such as a polyoxyethylene-polyoxypropylene condensate, (see patent document 4); a measurement method using a polyanion, such as dextran sulfate, a divalent metal salt, a specific nonionic surfactant, and albumin different from the albumin derived from a sample (see patent document 5); and a method for measuring HDL cholesterol in serum or plasma, which involves treating serum or plasma with a solution comprising a lipoprotein fractionating agent (a combination of a polyanion, such as dextran sulfate, and a divalent cation, such as magnesium ion), reacting the resultant mixture with a cholesterol esterase and a cholesterol oxidase in the presence of an anionic surfactant (an alkylsulfonic acid, or a bile acid or a derivative thereof) without subjecting the mixture to solid-liquid separation, and measuring a formed hydrogen peroxide (see patent document 6).

Known examples of methods for aggregating HDL cholesterol without aggregating lipoproteins other than HDL include: a method for measuring HDL cholesterol in a biological sample, which involves reacting the biological sample with pancreas-derived cholesterol esterase and cholesterol oxidase in the presence of a bile acid or a salt thereof and albumin, and measuring a compound consumed or formed by the enzymatic reaction (see patent document 7); and a method for measuring HDL cholesterol in a specimen, which involves reacting the specimen with a lipoprotein lipase preferentially acting on an HDL fraction and/or a cholesterol esterase and a cholesterol oxidase in the presence of a nonionic surfactant with an HLB value of 16 or more, having reaction selectivity on the HDL fraction (see patent document 8). Also known is a method which involves preferentially converting cholesterol in lipoproteins other than HDL into hydrogen peroxide with acyl polyoxyethylene sorbitan ester; eliminating a formed hydrogen peroxide; and then enzymatically measuring HDL cholesterol by adding a polyoxyethylene alkyl ether (see patent document 9).

Further, known are: a method for measuring HDL cholesterol in a specimen, which involves reacting the specimen with i) a cholesterol ester hydrolase and a cholesterol oxidase, or ii) a cholesterol ester hydrolase, an oxidized coenzyme, and a cholesterol dehydrogenase in an aqueous medium comprising a nonionic surfactant, a polyanion, and albumin, and measuring a formed hydrogen peroxide or reduced coenzyme (see patent document 10); and a method for measuring HDL cholesterol, which involves reacting a specimen with i) a cholesterol ester hydrolase and a cholesterol oxidase, or ii) a cholesterol ester hydrolase, an oxidized coenzyme, and a cholesterol dehydrogenase in an aqueous medium comprising a quaternary ammonium salt or amine having a specific structure and a polyanion, and measuring a formed hydrogen peroxide or reduced coenzyme (see patent document 11).

In a case where a specific substance in a specimen is measured by an optical technique, there is a problem is that for a specimen derived from a patient with liver/biliary tract disease, abnormal lipoprotein (LpX) in which phospholipids and free cholesterol are increased appears, and the LpX has an optical influence on the measurement system to provide an incorrect measurements. To avoid the optical influence, a method is commonly known which involves increasing the concentration of salts in the reaction solution to eliminate turbidity due to water-insoluble proteins. However, in HDL cholesterol measurement, the presence of a high concentration of salts may lead to a reduced specificity to HDL cholesterol and further a deactivation of contained enzymes.

PRIOR ART DOCUMENTS

Patent Documents

Patent Document 1: Japanese unexamined Patent Application Publication No. 62-69999
Patent Document 2: Japanese unexamined Patent Application Publication No. 63-126498
Patent Document 3: Japanese unexamined Patent Application Publication No. 8-131197
Patent Document 4: Japanese unexamined Patent Application Publication No. 8-201393
Patent Document 5: Japanese unexamined Patent Application Publication No. 9-285298
Patent Document 6: Japanese unexamined Patent Application Publication No. 8-116996
Patent Document 7: International Publication No. WO 97/40376
Patent Document 8: International Publication No. WO 00/52480
Patent Document 9: Japanese unexamined Patent Application Publication No. 9-299
Patent Document 10: International Publication No. WO 2004/035816
Patent Document 11: International Publication No. WO 2006/118199

SUMMARY OF THE INVENTION

Object to be Solved by the Invention

An object of the present invention is to provide a method, a reagent and a kit for measuring HDL cholesterol simply and accurately.

Means to Solve the Object

The present inventors have carried out intensive studies for solving the above object and have found that a cholesterol ester hydrolase and a cholesterol oxidase or a cholesterol dehydrogenase specifically act on HDL cholesterol under the coexistence of a specific nitrogen-containing substance having the structure of a pyridinium salt or a quaternary ammonium salt and a polyanion, thereby accomplishing the present invention.

Thus, the present invention relates to [1] to [13] blow.

[1] A method for measuring cholesterol in high-density lipoprotein in a specimen, comprising reacting the specimen with i) a cholesterol ester hydrolase and a cholesterol oxidase, or ii) a cholesterol ester hydrolase, an oxidized coenzyme, and a cholesterol dehydrogenase, in an aqueous medium comprising at least one substance selected from the group consisting of a substance represented by formula (I):

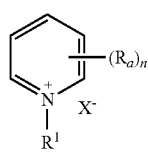

(wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion) and a substance represented by formula (II):

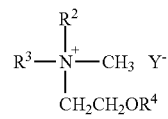

(wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, substituted or unsubstituted aryl, or substituted or unsubstituted alkyl; and $Y^-$ represents a monovalent anion), and a polyanion to form hydrogen peroxide or reduced coenzyme; and measuring the formed hydrogen peroxide or reduced coenzyme.

[2] The method according to [1], wherein the aqueous medium further comprises albumin.

[3] The method according to [1] or [2], wherein the polyanion is dextran sulfate or a salt thereof.

[4] A reagent for measuring cholesterol in high-density lipoprotein, comprising at least one substance selected from the group consisting of a substance represented by formula (I):

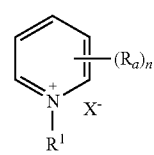

(wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion) and a substance represented by formula (II):

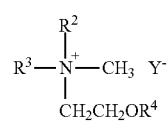

(wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, a substituted or unsubstituted aryl, or a substituted or unsubstituted alkyl; and $Y^-$ represents a monovalent anion), a polyanion, a cholesterol ester hydrolase, a cholesterol oxidase, and a reagent for measuring hydrogen peroxide.

[5] A reagent for measuring cholesterol in high-density lipoprotein, comprising at least one substance selected from the group consisting of a substance represented by formula (I):

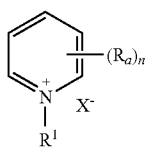

(wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion) and a substance represented by formula (II):

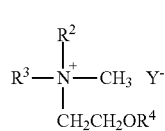

(wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, substituted or unsubstituted aryl, or a substituted or unsubstituted alkyl; and $Y^-$ represents a monovalent anion), a polyanion, a cholesterol ester hydrolase, a cholesterol dehydrogenase, and an oxidized coenzyme.

[6] The reagent according to [5], further comprising a reagent for measuring a reduced coenzyme.

[7] The reagent according to any one of [4] to [6], further comprising albumin.

[8] The reagent according to any one of [4] to [7], wherein the polyanion is dextran sulfate or a salt thereof.

[9] A kit for measuring cholesterol in high-density lipoprotein comprising a first reagent and a second reagent, wherein a substance represented by formula (I):

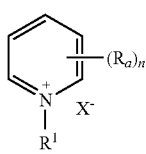

(wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion), a substance represented by formula (II):

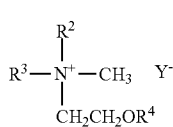

(wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, a substituted or unsubstituted aryl, or a substituted or unsubstituted alkyl; and $Y^-$ represents a monovalent anion), and a polyanion are comprised in the first reagent, a cholesterol oxidase is comprised in the second reagent, a reagent for measuring hydrogen peroxide is comprised in either the first or second reagent, or in both of the first and second reagents, and a cholesterol ester hydrolase is comprised in either the first or second reagent, or in both of the first and second reagents.

[10] A kit for measuring cholesterol in high-density lipoprotein comprising a first reagent and a second reagent, wherein a substance represented by formula (I):

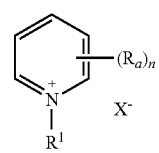

(wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion), a substance represented by formula (II):

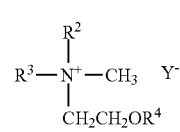

(wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, a substituted or unsubstituted aryl, or a substituted or unsubstituted alkyl; and $Y^-$ represents a monovalent anion), and a polyanion are comprised in the first reagent, a cholesterol dehydrogenase is comprised in the second reagent, an oxidized coenzyme is comprised in either the first or second reagent, or in both of the first and second reagents, and a cholesterol ester hydrolase is comprised in either the first or second reagent, or in both of the first and second reagents.

[11] The kit according to [10], further comprising a reagent for measuring a reduced coenzyme in either the first or second reagent, or in both of the first and second reagents.

[12] The kit according to any one of [9] to [11], further comprising albumin in either the first or second reagent, or in both of the first and second reagents.

[13] The kit according to any one of [9] to [12], wherein the polyanion is dextran sulfate or a salt thereof.

Effect of the Invention

In accordance with the present invention, there are provided a method, a reagent and a kit for measuring HDL cholesterol simply and accurately.

Mode of Carrying Out the Invention

The method for measuring HDL cholesterol according to the present invention is a method for specifically measuring HDL cholesterol without eliminating cholesterol in lipoproteins other than HDL.

Examples of the specimen used in the measurement method of the present invention include whole blood, plasma, serum, spinal fluid, saliva, amniotic fluid, urea, sweat, and pancreatic juice; plasma and serum are preferable.

The cholesterol ester hydrolase according to the present invention is not particularly limited so long as it is an enzyme having the capacity to hydrolyze a cholesterol ester; examples thereof include cholesterol esterase and lipoprotein lipase derived from an animal, a plant, or a microorganism; cholesterol esterase and lipoprotein lipase produced by a genetic engineering technique.

An unmodified cholesterol ester hydrolase as well as a chemically modified cholesterol ester hydrolase can be used as the cholesterol ester hydrolase. A commercially available cholesterol ester hydrolase can be used as a cholesterol ester hydrolase.

Examples of the commercially available cholesterol ester hydrolase include Cholesterol Esterase "Amano" 2 (CHE2; manufactured by Amano Enzyme Inc.), Cholesterol Esterase "Amano" 3 (CHE3; manufactured by Amano Enzyme Inc.), Cholesterol Esterase EST "Amano" 2 (manufactured by Amano Enzyme Inc.), Lipoprotein Lipase (LPL311; manufactured by Toyobo Co., Ltd.), Lipoprotein Lipase "Amano" 6 (LPL6; manufactured by Amano Enzyme Inc.), and Cholesterol Esterase [COE313 (chemically modified cholesterol esterase); manufactured by Toyobo Co., Ltd.]. In addition, in the present invention, two or more cholesterol ester hydrolases can also be used in combination.

Examples of the groups modifying a cholesterol ester hydrolase (chemically modifying groups) in chemically modifying the enzyme include a group comprising polyethylene glycol as a main component, a group having a copolymer of polypropylene glycol, a group comprising a water-soluble polysaccharide, a sulfopropyl group, a sulfobutyl group, a polyurethane group, and a group having a chelate function; a group comprising polyethylene glycol as a main component is preferable. Examples of the water-soluble polysaccharide include dextran, pullulan, and soluble starch.

Examples of the reagent for chemically modifying a cholesterol ester hydrolase (chemical modifiers) include a compound having both of the above chemically modifying groups and a functional group or structure capable of reacting with the amino group, the carboxyl group, the sulfhydryl group, or the like of the enzyme. Examples of the functional group or the structure capable of reacting with the amino group of the enzyme include a carboxyl group, an active ester group (e.g., N-hydroxysuccinimide), an acid anhydride, an acid chloride, an aldehyde, an epoxide group, 1,3-propanesultone, and 1,4-butanesultone. Examples of the functional group or the structure capable of reacting with the carboxyl group of the enzyme include an amino group. Examples of the group or the structure having reactivity with the sulfhydryl group of the enzyme include a maleimide group, a disulfide, and an α-halo ester (e.g., α-iodo ester).

A commercially available chemical modifier can be used as a chemical modifier. Examples of the commercially available chemical modifier include Sunbright ME-50CS, Sunbright MEAC-50HS, and Sunbright MEC-50HS (all are manufactured by NOF Corporation), which have a group comprising polyethylene glycol as a main component and an N-hydroxysuccinimide group; Sunbright AKM series (e.g., Sunbright AKM-1510), Sunbright ADM series, and Sunbright ACM series (all are manufactured by NOF Corporation), which have a group comprising a polyalkylene glycol as a main component and an acid anhydride structure; EPDX-3400 and M-EPDX-5000 (both are manufactured by Sheawater Polymers, Inc.), which have a group comprising polyethylene glycol as a main component and an epoxide group; diethylenetriamine-N,N,N",N"-pentaacetic anhydride (DTPA anhydride; manufactured by Dojindo Laboratories), which has a group having a chelate function and an acid anhydride structure.

The method for chemically modifying a cholesterol ester hydrolase is not particularly limited; for example, the modification can be carried out by dissolving a cholesterol ester hydrolase in a buffer solution of pH 8.0 or more (e.g., HEPES buffer solution), adding a 0.01- to 500-fold molar amount of a chemical modifier at 0 to 5° C., and stirring the resultant for 5 minutes to 5 hours. As a chemically modified cholesterol ester hydrolase used in the present invention, this reaction solution itself can be used, and optionally a solution from which an unreacted chemical modifier and the like are removed using an ultrafiltration membrane or the like can be used.

The concentration of the cholesterol ester hydrolase used in the method for this reaction is not particularly limited so long as it is a concentration that enables the measurement of HDL cholesterol according to the present invention; it is preferably a concentration of 0.01 to 200 U/mL, more preferably 0.02 to 100 U/mL, in the reaction solution.

The cholesterol oxidase according to the present invention is not particularly limited so long as it is an enzyme having the capacity to oxidize cholesterol to form hydrogen peroxide; examples thereof include: cholesterol oxidase derived from an animal, a plant, a microorganism or the like. There can also be used commercially available enzymes such as Cholesterol Oxidase "Amano" I (CHOD1; manufactured by Amano Enzyme Inc.), Cholesterol Oxidase (CHO-PEL; manufactured by Kikkoman Corporation), and Cholesterol Oxidase (C00321; manufactured by Toyobo Co., Ltd.). In the present invention, two or more cholesterol oxidases may also be used in combination.

The cholesterol oxidase may be an unmodified enzyme or a chemically modified enzyme. The chemically modified cholesterol oxidase can be prepared, for example, by the above chemical modification method using any of the above chemical modifiers.

The concentration of the cholesterol oxidase used in the method for the reaction is not particularly limited so long as it is a concentration that enables the measurement of HDL cholesterol according to the present invention; it is preferably a concentration of 0.01 to 200 U/mL, more preferably 0.02 to 100 U/mL, in the reaction solution.

The cholesterol dehydrogenase according to the present invention is not particularly limited so long as it is an enzyme having the capacity to oxidize cholesterol in the presence of an oxidized coenzyme to form a reduced coenzyme; examples thereof include: cholesterol dehydrogenase derived from an animal, a plant, or a microorganism; cholesterol dehydrogenase produced by a genetic engineering technique. Commercially available enzymes, such as Cholesterol Dehydrogenase "Amano" 5 (CHDH5; manufactured by Amano Enzyme Inc.), may also be used. In the present invention, two or more cholesterol dehydrogenases may also be used in combination. The cholesterol dehydrogenase may be an unmodified enzyme or a chemically modified enzyme.

The chemically modified cholesterol dehydrogenase can be prepared, for example, by the above chemical modification method using any of the above chemical modifiers.

The concentration of the cholesterol dehydrogenase used in the method for the reaction is not particularly limited so long as it is a concentration that enables the measurement of HDL cholesterol according to the present invention; it is preferably a concentration of 0.01 to 200 U/mL, more preferably 0.02 to 100 U/mL, in the reaction solution.

An oxidized coenzyme is used in the measurement method using a cholesterol dehydrogenase according to the present invention. Examples of the oxidized coenzyme include $NAD^+$, $NADP^+$, thio-$NAD^+$, and thio-$NADP^+$.

According to the present invention, a substance represented by general formula (I):

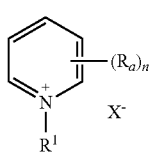
(I)

(wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion) [hereinafter referred to as compound (I)], and a substance represented by general formula (II):

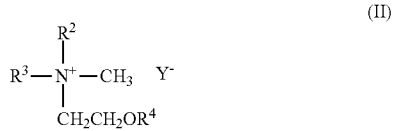
(II)

(wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, a substituted or unsubstituted aryl, or a substituted or unsubstituted alkyl; and $Y^-$ represents a monovalent anion) [hereinafter referred to as compound (II)] are used together with a polyanion.

In $R^1$, examples of the alkyl in the substituted or unsubstituted alkyl having 8 to 14 carbon atoms include octyl, nonyl, decyl, undecyl, dodecyl (lauryl), tridecyl, and tetradecyl; preferred is alkyl having 12 to 14 carbon atoms.

In $R^1$, examples of the alkenyl in the substituted or unsubstituted alkenyl having 8 to 14 carbon atoms include octenyl, nonenyl, decenyl, undecenyl, dodecenyl, tridecenyl, and tetradecenyl; preferred is alkenyl having 12 to 14 carbon atoms.

In $R^1$, examples of the substituent in the substituted alkyl having 8 to 14 carbon atoms and the substituted alkenyl having 8 to 14 carbon atoms include a phenyl group, a hydroxyl group, a sulfo group, a cyano group, and a halogen atom. Examples of the halogen atom include a chlorine atom, a bromine atom, and an iodine atom.

In $R_a$, examples of the alkyl in the substituted or unsubstituted alkyl include alkyl having 1 to 20 carbon atoms. Examples of the alkyl having 1 to 20 carbon atoms include methyl, ethyl, propyl, butyl, pentyl, hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl.

In $R_a$, examples of the alkenyl in the substituted or unsubstituted alkenyl include alkenyl having 2 to 20 carbon atoms. Examples of the alkenyl having 2 to 20 carbon atoms include vinyl, propenyl, allyl, butenyl, pentenyl, hexenyl, heptenyl, octenyl, nonenyl, decenyl, undecenyl, dodecenyl, tetradecenyl, pentadecenyl, hexadecenyl, heptadecenyl, octadecenyl, oleyl, nonadecenyl, and icosenyl.

In $R_a$, examples of the substituent in the substituted alkyl and the substituted alkenyl include a phenyl group, a hydroxyl group, a sulfo group, a cyano group, and a halogen atom. Examples of the phenyl group-substituted alkyl include benzyl and 1-phenylethyl. Examples of the halogen atom include a chlorine atom, a bromine atom, and an iodine atom.

In a case where two or more substituents are on a pyridine ring, these substituents may be the same or different. $X^-$ in the compound (I) represents a monovalent anion. Examples of the monovalent anion include halogen ion, $OH^-$, $PF_6^-$, $BF_4^-$, $CH_3CH_2OSO_3^-$, and $(CF_3SO_2)_2N^-$. Examples of the halogen ion include $Cl^-$, $Br^-$, and $I^-$.

As a compound (I), is preferably a compound (I) in which $R^1$ is substituted or unsubstituted alkyl or alkenyl having 12 to 14 carbon atoms and $R_a$ is a hydrogen atom.

Specific examples (products) of the Compound (I) include lauryl pyridinium chloride and cetyl pyridinium chloride (both are manufactured by Tokyo Chemical Industry Co., Ltd.).

In $R^2$, examples of the alkyl in the substituted or unsubstituted alkyl having 6 to 30 carbon atoms include hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl, and triacontyl; preferred is alkyl having 8 to carbon atoms, more preferably alkyl having 8 to 18 carbon atoms.

In $R^2$, examples of the alkenyl in the substituted or unsubstituted alkenyl having 6 to 30 carbon atoms include hexenyl, heptenyl, octenyl, nonenyl, decenyl, undecenyl, dodecenyl, tridecenyl, tetradecenyl, pentadecenyl, hexadecenyl, heptadecenyl, octadecenyl, oleyl, nonadecenyl, icosenyl, heneicosenyl, docosenyl, tricosenyl, tetracosenyl, pentacosenyl, hexacosenyl, heptacosenyl, octacosenyl, nonacosenyl, and triaconsenyl; preferred is alkenyl having 8 to 20 carbon atoms, more preferably alkenyl having 8 to 18 carbon atoms.

In $R^2$, examples of the substituent in the substituted alkyl having 6 to 30 carbon atoms and the substituted alkenyl having 6 to 30 carbon atoms include a phenyl group, a hydroxyl group, an alkoxyl group, a sulfo group, a cyano group, and a halogen atom. Examples of the phenyl group-substituted alkyl include benzyl and 1-phenylethyl. Examples of the halogen atom include a chlorine atom, a bromine atom, and an iodine atom.

In $R^3$, examples of the alkyl in the substituted or unsubstituted alkyl having 1 to 6 carbon atoms include methyl, ethyl, propyl, butyl, pentyl, and hexyl; preferred is alkyl having 1 to 4 carbon atoms.

In $R^3$, examples of the alkenyl in the substituted or unsubstituted alkenyl having 2 to 6 carbon atoms include vinyl, propenyl, allyl, butenyl, pentenyl, and hexenyl; preferred is alkenyl having 2 to 4 carbon atoms.

In $R^3$, examples of the substituent in the substituted alkyl having 1 to 6 carbon atoms and the substituted alkenyl having 2 to 6 carbon atoms include a phenyl group, a hydroxyl group, an alkoxyl group, a sulfo group, a cyano group, and a halogen atom. Examples of the phenyl group-substituted alkyl include benzyl and 1-phenylethyl. Examples of the halogen atom include a chlorine atom, a bromine atom, and an iodine atom.

In $R^4$, examples of the aryl in the substituted or unsubstituted aryl include phenyl and naphthyl.

In $R^4$, examples of the alkyl in the substituted or unsubstituted alkyl include alkyl having 1 to 20 carbon atoms. Examples of the alkyl having 1 to 20 carbon atoms include the aforementioned alkyl having 1 to 20 carbon atoms.

In $R^4$, examples of the substituent in the substituted aryl and the substituted alkyl include a phenyl group, a hydroxyl group, an alkoxyl group, a sulfo group, a cyano group, and a halogen atom. Examples of the phenyl group-substituted alkyl include benzyl and 1-phenylethyl. Examples of the halogen atom include a chlorine atom, a bromine atom, and an iodine atom.

$Y^-$ in the compound (II) represents a monovalent anion. Examples of the monovalent anion include halogen ion, $OH^-$, $PF_6^-$, $BF_4^-$, $CH_3CH_2OSO_3^-$, and $(CF_3SO_2)_2N^-$. Examples of the halogen ion include $Cl^-$, $Br^-$, and $I^-$.

As a compound (II), is preferably a compound (II) in which $R^2$ is a substituted or unsubstituted alkyl or alkenyl having 8 to 18 carbon atoms; $R^3$ is a substituted or unsubstituted alkyl having 1 to 4 carbon atoms or a substituted or unsubstituted alkenyl having 2 to 4 carbon atoms; and $R^4$ is a hydrogen atom, a substituted or unsubstituted aryl, or a substituted or unsubstituted alkyl.

Specific examples (products) of the compound (II) include Ethoquad C/12 coconut oil alkyl bis(2-hydroxyethyl)methylammonium chloride; manufactured by Lion Corporation, Ethoquad C/25 [polyoxyethylene coconut oil alkyl methylammonium chloride; manufactured by Lion Corporation], and domiphen bromide [dimethyldodecyl(2-phenoxyethyl)ammonium bromide; manufactured by Tokyo Chemical Industry Co., Ltd.]. The coconut oil alkyl in Ethoquad C/12 and Ethoquad C/25 is alkyl having 8 to 18 carbon atoms, and examples of the alkyl having 8 to 18 carbon atoms include octyl, nonyl, decyl, undecyl, dodecyl (lauryl), tridecyl, tetradecyl (myristyl), pentadecyl, hexadecyl (cetyl), heptadecyl, and octadecyl (stearyl).

According to the method for measuring HDL cholesterol of the present invention, a concentration of the compound (I) and the compound (II) in the reaction solution is not particularly limited so long as it is a concentration that enables the method for measuring HDL cholesterol of the present invention; it is usually 0.001 to 3%, preferably 0.002 to 0.3%.

A polyanion used in the present invention is not particularly limited so long as it is a polyanion that enables the method for measuring HDL cholesterol of the present invention. Examples thereof include dextran sulfate or a salt thereof, heparin or a salt thereof, phosphotungstic acid or a salt thereof, sulfated cyclodextrin or a salt thereof, sulfated oligosaccharide or a salt thereof, and carrageenan; preferred is dextran sulfate or a salt thereof. Examples of the dextran sulfate include dextran sulfate having a molecular weight of 40,000, 80,000, 200,000, 500,000, 1,000,000, or 2,000,000. Examples of the sulfated oligosaccharide include sulfated agarose, sulfated trehalose, and chondroitin sulfate. Examples of the salt include a sodium salt, a potassium salt, a lithium salt, an ammonium salt, and a magnesium salt. In the present invention, two or more polyanions may be used.

According to the method for measuring HDL cholesterol of the present invention, the concentration of the polyanion in the reaction solution is not particularly limited so long as it is a concentration that enables the method for measuring HDL cholesterol of the present invention; it is usually 0.001 to 10%, preferably 0.01 to 1%.

Alubmin used in the present invention is not particularly limited so long as it is albumin that enables the method for measuring HDL cholesterol of the present invention. Examples thereof include bovine, ovine, or human albumin; preferred is bovine serum albumin (hereinafter abbreviated as BSA). Albumin produced by a genetic engineering technique may also be used. In the present invention, two or more albumins may also be used in combination.

In the method for measuring HDL cholesterol of the present invention, a concentration of albumin in the reaction solution is not particularly limited so long as it is a concentration that enables the method for measuring HDL cholesterol of the present invention; it is usually 0.001 to 10%, preferably 0.01 to 1%.

An aqueous medium used in the method for measuring HDL cholesterol of the present invention is not particularly limited so long as it is an aqueous medium that enables the method for measuring HDL cholesterol of the present invention. Examples thereof include a deionized water, a distilled water, and a buffer solution; preferred is a buffer solution.

Examples of the buffer used in the buffer solution include a tris(hydroxymethyl)aminomethane buffer, a phosphate buffer, a borate buffer, and a Good's buffer. Examples of the Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

A concentration of the buffer solution is not particularly limited so long as it is a concentration suitable for the measurement; it is usually 0.001 to 2.0 mol/L, preferably 0.005 to 1.0 mol/L.

The method, the reagent and the kit for measuring HDL cholesterol according to the present invention will be specifically described below.

(Method for Measuring HDL Cholesterol)

Examples of the method for measuring HDL cholesterol according to the present invention include methods in the following embodiments.

Measurement Method 1

The concentration of HDL cholesterol in a specimen can be determined by:

(1) reacting the specimen with a cholesterol ester hydrolase and a cholesterol oxidase, or a cholesterol ester hydrolase, an oxidized coenzyme, and a cholesterol dehydrogenase, in an aqueous medium comprising the compound (I) or the compound (II) and a polyanion to form hydrogen peroxide or a reduced coenzyme;

(2) measuring the formed hydrogen peroxide or reduced coenzyme; and (3) calculating the concentration of HDL cholesterol in the specimen from the value measured in (2) and a previously-prepared calibration curve showing the relationship between HDL cholesterol concentrations and measured values of hydrogen peroxide or reduced coenzyme.

Measurement Method 2

The concentration of HDL cholesterol in a specimen can be determined by:

(1) reacting the specimen with a cholesterol ester hydrolase and a cholesterol oxidase, or a cholesterol ester hydrolase, an oxidized coenzyme, and a cholesterol dehydrogenase, in an aqueous medium comprising the compound (I) or the compound (II), a polyanion, and albumin to form hydrogen peroxide or a reduced coenzyme;

(2) measuring the formed hydrogen peroxide or reduced coenzyme; and (3) calculating the concentration of HDL cholesterol in the specimen from the value measured in (2) and a previously-prepared calibration curve showing the relationship between HDL cholesterol concentrations and measured values of hydrogen peroxide or reduced coenzyme.

In this measurement method, the reaction of (1) is carried out, for example, at 10 to 50° C., preferably 20 to 40° C., for 1 to 60 minutes, preferably 2 to 30 minutes.

The amount of the formed hydrogen peroxide may also, for example, be measured using a reagent for measuring hydrogen peroxide, while it may be directly measured using an electrode for hydrogen peroxide detection. The reagent for measuring hydrogen peroxide is a reagent for converting the formed hydrogen peroxide to a detectable substance. Examples of the detectable substance include a dye and a luminescence; preferred is a dye. In a case where the detectable substance is a dye, the reagent for measuring hydrogen peroxide comprises an oxidative coloring-type chromogen and a peroxidative substance, such as a peroxidase. Examples of the oxidative coloring-type chromogen include oxidative coloring-type chromogens to be described later. In a case where the detectable substance is a luminescence, the reagent for measuring hydrogen peroxide comprises a chemiluminescent substance. Examples of the chemiluminescent substance include luminol, isoluminol, lucigenin, and an acridinium ester.

In a case where a reagent comprising an oxidative coloring-type chromogen and a peroxidative substance, such as a peroxidase, is used as a reagent for measuring hydrogen peroxide, hydrogen peroxide can be determined by reacting the hydrogen peroxide with an oxidative coloring-type chromogen in the presence of a peroxidative substance to form a dye and measuring the formed dye. In a case where a reagent for measuring hydrogen peroxide comprising a chemiluminescent substance is used, hydrogen peroxide can be determined by reacting the hydrogen peroxide with the chemiluminescent substance to generate photon and measuring the generated photon.

Examples of the oxidative coloring-type chromogen include a leuco-type chromogen and an oxidative coupling coloring-type chromogen.

The leuco-type chromogen is a substance that is converted to a dye by itself in the presence of hydrogen peroxide and a peroxidative substance such as a peroxidase. Specific examples thereof include 10-N-carboxymethylaminocarbonyl-3,7-bis(dimethylamino)-10-phenothiazine (CCAP), 10-N-methylcarbamoyl-3,7-bis(dimethylamino)-10-phenothiazine (MCDP), N-(carboxymethylaminocarbonyl)-4,4'-bis(dimethylamino)diphenylamine sodium salt (DA-64), 10-N-carboxymethylaminocarbonyl-3,7-bis(dimethylamino)-10-phenothiazine sodium salt (DA-67), 4,4'-bis(dimethylamino)diphenylamine, and bis[3-bis(4-chlorophenyl)methyl-4-dimethylaminophenyl]amine (BCMA).

The oxidative coupling coloring-type chromogen is a substance that forms a dye by oxidative-coupling of two compounds in the presence of hydrogen peroxide and a peroxidative substance such as a peroxidase.

Examples of the combination of the two compounds include a combination of a coupler and an aniline and a combination of a coupler and a phenol. Examples of the coupler include 4-aminoantipyrine (4-AA) and 3-methyl-2-benzothiazolinone hydrazine. Examples of the aniline include N-(3-sulfopropyl)aniline, N-ethyl-N-(2-hydroxy-3-sulfopropyl)-3-methylaniline (TOGS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, and N-ethyl-N-(2-hydroxy-3-sulfopropyl)-4-fluoro-3,5-dimethoxyaniline (F-DAOS). Examples of the phenol include phenol, 4-chlorophenol, 3-methylphenol, and 3-hydroxy-2,4,6-triiodobenzoic acid (HTIB).

In the measurement of hydrogen peroxide, the concentration of the peroxidative substance is not particularly limited so long as it is a concentration suitable for the measurement; in a case where a peroxidase is used as the peroxidative substance, it is usually 1 to 100 kU/L. The concentration of the oxidative coloring-type chromogen is not particularly limited so long as it is a concentration suitable for the measurement; it is usually 0.01 to 10 g/L.

Methods for measuring the reduced coenzyme include a method which comprises measuring the absorbance of the formed reduced coenzyme and a method using a reagent for measuring the reduced coenzyme. In the method comprising measuring the absorbance of the reduced coenzyme, the absorbance is usually 300 to 500 nm, preferably 330 to 400 nm, more preferably around 340 nm. The reagent for measuring the reduced coenzyme is a reagent for converting the formed reduced coenzyme to a detectable substance. Examples of the detectable substance include a dye. Examples of the reagent for measuring the reduced coenzyme in a case where the detectable substance is a dye include a reagent comprising a diaphorase, an electron carrier, and a reductive coloring-type chromogen. Examples of the electron carrier include 1-methoxy-5-methylphenazinium methylsulfate. In a case where the reagent comprising a diaphorase, an electron carrier, and a reductive coloring-type chromogen is used as a reagent for measuring a reduced coenzyme, the reduced coenzyme can be determined by determining the dye formed by the conversion of the reductive coloring-type chromogen.

Examples of the reductive coloring-type chromogen include 3-(4,5-dimethyl-2-thiazolyl)-2,5-diphenyl-2H-tetrazolium bromide (MTT), 2-(4-iodophenyl)-3-(4-nitrophenyl)-5-(2,4-disulfophenyl)-2H-tetrazolium monosodium salt (WST-1), and 2-(4-iodophenyl)-3-(2,4-dinitrophenyl)-5-(2,4-disulfophenyl)-2H-tetrazolium monosodium salt (WST-3).

(Reagent for Measuring HDL Cholesterol)

The reagent for measuring HDL cholesterol according to the present invention can be used for the method for measuring HDL cholesterol according to the present invention.

Examples of the reagent for measuring HDL cholesterol according to the present invention include reagents in the following embodiments, which are not intended in any way to limit the scope of the present invention.

Reagent 1

A reagent comprising at least one substance selected from the group consisting of the compound (I) and the compound (II), a polyanion, a cholesterol ester hydrolase, a cholesterol oxidase, and a reagent for measuring hydrogen peroxide.

Reagent 2

A reagent comprising at least one substance selected from the group consisting of the compound (I) and the compound (II), a polyanion, a cholesterol ester hydrolase, an oxidized coenzyme, and a cholesterol dehydrogenase.

Reagent 3

A reagent comprising at least one substance selected from the group consisting of the compound (I) and the compound (II), a polyanion, a cholesterol ester hydrolase, an oxidized coenzyme, a cholesterol dehydrogenase, and a reagent for measuring a reduced coenzyme.

Reagent 4

A reagent comprising at least one substance selected from the group consisting of the compound (I) and the compound (II), a polyanion, albumin, a cholesterol ester hydrolase, a cholesterol oxidase, and a reagent for measuring hydrogen peroxide.

Reagent 5

A reagent comprising at least one substance selected from the group consisting of the compound (I) and the compound (II), a polyanion, albumin, a cholesterol ester hydrolase, an oxidized coenzyme, and a cholesterol dehydrogenase.

Reagent 6

A reagent comprising at least one substance selected from the group consisting of the compound (I) and the compound (II), a polyanion, albumin, a cholesterol ester hydrolase, an oxidized coenzyme, a cholesterol dehydrogenase, and a reagent for measuring a reduced coenzyme.

(Kit for Measuring HDL Cholesterol)

The reagent for measuring HDL cholesterol according to the present invention may be preserved, distributed, and used in the form of a kit. The form of the kit is not particularly limited; it may be a two-reagent system, a three-reagent system, or the like; a two-reagent system is preferable. The kit for measuring HDL cholesterol according to the present invention can be used for the method for measuring HDL cholesterol according to the present invention.

In the two-reagent system kit for measuring HDL cholesterol, consisting of a first reagent and a second reagent, a cholesterol ester hydrolase and a cholesterol oxidase or the cholesterol dehydrogenase may be separately contained in the first reagent and the second reagent or contained together in the second reagent; in a case where they are separately contained in the first reagent and the second reagent, an embodiment is preferable in which a cholesterol ester hydrolase is contained in the first reagent and a cholesterol oxidase or a cholesterol dehydrogenase is contained in the second reagent. An oxidized coenzyme used in the measurement method using a cholesterol dehydrogenase may be contained in either the first or second reagent, or in both of the first and second reagents.

At least one substance selected from the group consisting of the compound (I) and the compound (II) may be contained in either the first or second reagent, or in both of the first and second reagents; the substance is preferably contained in the first reagent. The polyanion may be contained in either the first or second reagent, or in both of the first and second reagents; it is preferably contained in the first reagent. Albumin may be contained in either the first or second reagent, or in both of the first and second reagents; it is preferably contained in the first reagent.

The reagent for measuring hydrogen peroxide may be contained in either the first or second reagent, or in both of the first and second reagent; in a case where the reagent comprises oxidative coupling-type chromogen, preferred is an embodiment in which one of a pair of oxidative coupling-type chromogens is contained in the first reagent and the other is contained in the second reagent, that is, an embodiment in which the reagent for measuring hydrogen peroxide is contained in both of the first and second reagents. The reagent for measuring a reduced coenzyme may be contained in either the first or second reagent, or in both of the first and second reagents; it is preferably contained in both of the first and second reagents.

Examples of the kit for measuring HDL cholesterol according to the present invention include kits in the following embodiments, which are not intended in any way to limit the scope of the present invention.

Kit 1

First Reagent

At least one substance selected from the group consisting of the compound (I) and the compound (II), a polyanion, a reagent for measuring hydrogen peroxide, and a cholesterol ester hydrolase Second Reagent A reagent for measuring hydrogen peroxide and a cholesterol oxidase Kit 2

First Reagent

At least one substance selected from the group consisting of the compound (I) and the compound (II), a polyanion, and a reagent for measuring hydrogen peroxide Second Reagent A reagent for measuring hydrogen peroxide, a cholesterol ester hydrolase, and a cholesterol oxidase Kit 3

First Reagent

At least one substance selected from the group consisting of the compound (I) and the compound (II), a polyanion, an oxidized coenzyme, and a cholesterol ester hydrolase Second Reagent A cholesterol dehydrogenase Kit 4

First Reagent

At least one substance selected from the group consisting of the compound (I) and the compound (II), a polyanion, and an oxidized coenzyme Second Reagent A cholesterol ester hydrolase and a cholesterol Dehydrogenase Kit 5

First Reagent

At least one substance selected from the group consisting of the compound (I) and the compound (II), a polyanion, an oxidized coenzyme, a reagent for measuring a reduced coenzyme, and a cholesterol ester hydrolase Second Reagent A reagent for measuring a reduced coenzyme and a cholesterol dehydrogenase Kit 6

First Reagent

At least one substance selected from the group consisting of the compound (I) and the compound (II), a polyanion, an oxidized coenzyme, and a reagent for measuring a reduced coenzyme Second Reagent A reagent for measuring a reduced coenzyme, a cholesterol ester hydrolase, and a cholesterol dehydrogenase Kit 7

First Reagent

At least one substance selected from the group consisting of the compound (I) and the compound (II), a polyanion, albumin, a reagent for measuring hydrogen peroxide, and a cholesterol ester hydrolase Second Reagent A reagent for measuring hydrogen peroxide and a cholesterol oxidase Kit 8

First Reagent

At least one substance selected from the group consisting of the compound (I) and the compound (II), a polyanion, albumin, and a reagent for measuring hydrogen peroxide Second Reagent A reagent for measuring hydrogen peroxide, a cholesterol ester hydrolase, and a cholesterol oxidase Kit 9

First Reagent

At least one substance selected from the group consisting of the compound (I) and the compound (II), a polyanion, albumin, an oxidized coenzyme, and a cholesterol ester hydrolase Second Reagent A cholesterol dehydrogenase Kit 10

First Reagent

At least one substance selected from the group consisting of the compound (I) and the compound (II), a polyanion, albumin, and an oxidized coenzyme Second Reagent A cholesterol ester hydrolase and a cholesterol dehydrogenase Kit 11

First Reagent

At least one substance selected from the group consisting of the compound (I) and the compound (II), a polyanion, albumin, an oxidized coenzyme, a reagent for measuring a reduced coenzyme, and a cholesterol ester hydrolase Second Reagent A reagent for measuring a reduced coenzyme and a cholesterol dehydrogenase Kit 12

First Reagent

At least one substance selected from the group consisting of the compound (I) and the compound (II), a polyanion, albumin, an oxidized coenzyme, and a reagent for measuring a reduced coenzyme Second Reagent A reagent for measuring a reduced coenzyme, a cholesterol ester hydrolase, and a cholesterol dehydrogenase In the reagent and the kit for measuring HDL cholesterol according to the present invention, the compound (I), the compound (II), a polyanion, albumin, a cholesterol ester hydrolase, a cholesterol oxidase, a cholesterol dehydrogenase, an oxidized coenzyme, a reagent for measuring hydrogen peroxide, and a reagent for measuring a reduced coenzyme mentioned above in the method for measuring HDL cholesterol according to the present invention can be used.

The reagent and the kit for measuring HDL cholesterol according to the present invention may comprise an aqueous medium, a stabilizer, a preservative, an interference inhibitor, a reaction promoter, and the like, if necessary. Examples of the aqueous medium include the aforementioned aqueous media. Examples of the stabilizer include ethylenediaminetetraacetic acid (EDTA), sucrose, and calcium chloride. Examples of the preservative include sodium azide and an antibiotic. Examples of the interference inhibitor include an ascorbate oxidase for eliminating the influence of ascorbic acid. Examples of the reaction promoter include enzymes such as colipase and phospholipase, and salts such as sodium sulfate and sodium chloride.

The reagent and the kit for measuring HDL cholesterol according to the present invention may be in freeze-dried form or in a state dissolved in an aqueous medium. In a case where HDL cholesterol in a specimen is measured using the reagent in freeze-dried form, the reagent is used after being dissolved in an aqueous medium. Examples of the aqueous medium used for dissolving the reagent in freeze-dried form include the aforementioned aqueous media.

The amount of the cholesterol ester hydrolase, the cholesterol oxidase, and the cholesterol dehydrogenase in the reagent and the kit for measuring HDL cholesterol according to the present invention is usually an amount such that the concentration thereof in a state dissolved in an aqueous medium is 0.01 to 1,200 U/mL, preferably 0.02 to 600 U/mL.

The amount of the compound (I) or the compound (II) in the reagent and the kit for measuring HDL cholesterol according to the present invention is usually an amount such that the concentration thereof in a state dissolved in an aqueous medium is 0.001 to 10%, preferably 0.002 to 1%. The amount of the polyanion in the reagent and the kit for measuring HDL cholesterol according to the present invention is usually an amount such that the concentration thereof in a state dissolved in an aqueous medium is 0.001 to 30%, preferably 0.01 to 3%.

The amount of albumin in the reagent and the kit for measuring HDL cholesterol according to the present invention is usually an amount such that the concentration thereof in a state dissolved in an aqueous medium is 0.001 to 30%, preferably 0.01 to 3%.

The present invention will be described below in detail with reference to Examples, which are not intended in any way to limit the scope of the present invention. In these Examples, reagents and enzymes from the following manufacturers were used. HEPES (manufactured by Calbiochem), EMSE (manufactured by Daito Chemix Corporation), sodium dextran sulfate (molecular weight: 500,000) (manufactured by PK Chemicals A/S), bovine serum albumin (BSA; manufactured by Millipore Corporation), sodium sulfate (manufactured by Kanto Chemical Co., Inc.), 4-AA (manufactured by Saikyo Kasei K.K.), peroxidase (manufactured by Toyobo Co., Ltd.), EST "Amano" 2 (cholesterol ester hydrolase; manufactured by Amano Enzyme Inc.), CHO-PEL (cholesterol oxidase; manufactured by Kikkoman Corporation), laurylpyridinium chloride (manufactured by Tokyo Chemical Industry Co., Ltd.), domiphen bromide (manufactured by Tokyo Chemical Industry Co., Ltd.), Ethoquad C/12 (manufactured by Lion Corporation), Ethoquad C/25 (manufactured by Lion Corporation), and Cation BB (dodecyltrimethyl ammonium chloride; manufactured by NOF Corporation).

EXAMPLES

Example 1

A kit for measuring HDL cholesterol consisting of the following first reagent and second reagent was prepared.

First Reagent (Reagent A)

| | |
|---|---|
| HEPES (pH 7.5) | 10 mmol/L |
| EMSE | 0.3 g/L |
| Sodium sulfate | 5.0 g/L |
| Sodium dextran sulfate (molecular weight: 500,000) | 0.2 g/L |
| BSA | 2.0 g/L |
| Peroxidase | 10 kU/L |
| Laurylpyridinium chloride | 0.025 g/L |

Second Reagent (Reagent a)

| | |
|---|---|
| HEPES (pH 7.0) | 10 mmol/L |
| 4-AA | 0.3 g/L |
| Peroxidase | 20 kU/L |
| EST "Amano" 2 | 100 kU/L |
| CHO-PEL | 1.2 kU/L |

Example 2

A kit for measuring HDL cholesterol consisting of the following first reagent and second reagent was prepared.

First Reagent (Reagent B)

| | |
|---|---|
| HEPES (pH 7.5) | 10 mmol/L |
| EMSE | 0.3 g/L |
| Sodium sulfate | 5.0 g/L |
| Sodium dextran sulfate (molecular weight: 500,000) | 0.2 g/L |
| BSA | 2.0 g/L |
| Peroxidase | 10 kU/L |
| Domiphen bromide | 0.03 g/L |

Second Reagent (Reagent a)

| | |
|---|---|
| HEPES (pH 7.0) | 10 mmol/L |
| 4-AA | 0.3 g/L |
| Peroxidase | 20 kU/L |
| EST "Amano" 2 | 100 kU/L |
| CHO-PEL | 1.2 kU/L |

Example 3

A kit for measuring HDL cholesterol consisting of the following first reagent and second reagent was prepared.

First Reagent (Reagent C)

| | |
|---|---|
| HEPES (pH 7.5) | 10 mmol/L |
| EMSE | 0.3 g/L |
| Sodium sulfate | 5.0 g/L |
| Sodium dextran sulfate (molecular weight: 500, 000) | 0.2 g/L |
| BSA | 2.0 g/L |
| Peroxidase | 10 kU/L |
| Ethoquad C/12 | 0.035 g/L |

Second Reagent (Reagent a)

| | |
|---|---|
| HEPES (pH 7.0) | 10 mmol/L |
| 4-AA | 0.3 g/L |
| Peroxidase | 20 kU/L |
| EST "Amano" 2 | 100 kU/L |
| CHO-PEL | 1.2 kU/L |

Example 4

A kit for measuring HDL cholesterol consisting of the following first reagent and second reagent was prepared.

First Reagent (Reagent D)

| | |
|---|---|
| HEPES (pH 7.5) | 10 mmol/L |
| EMSE | 0.3 g/L |
| Sodium sulfate | 5.0 g/L |
| Sodium dextran sulfate (molecular weight: 500,000) | 0.2 g/L |
| BSA | 2.0 g/L |
| Peroxidase | 10 kU/L |
| Ethoquad C/25 | 0.075 g/L |

Second Reagent (Reagent a)

| | |
|---|---|
| HEPES (pH 7.0) | 10 mmol/L |
| 4-AA | 0.3 g/L |
| Peroxidase | 20 kU/L |
| EST "Amano" 2 | 100 kU/L |
| CHO-PEL | 1.2 kU/L |

Comparative Example 1

Kit for Measuring HDL Cholesterol

A kit for measuring HDL cholesterol consisting of the following first reagent and second reagent was prepared.

First Reagent (Reagent E)

| | |
|---|---|
| HEPES (pH 7.5) | 10 mmol/L |
| EMSE | 0.3 g/L |
| Sodium sulfate | 5.0 g/L |
| Sodium dextran sulfate (molecular weight: 500,000) | 0.2 g/L |
| BSA | 2.0 g/L |
| Peroxidase | 10 kU/L |

Second Reagent (Reagent a)

| HEPES (pH 7.0) | 10 mmol/L |
|---|---|
| 4-AA | 0.3 g/L |
| Peroxidase | 20 kU/L |
| EST "Amano" 2 | 100 kU/L |
| CHO-PEL | 1.2 kU/L |

Comparative Example 2

Kit for Measuring HDL Cholesterol

A kit for measuring HDL cholesterol consisting of the following first reagent and second reagent was prepared.

First Reagent (Reagent F)

| HEPES (pH 7.5) | 10 mmol/L |
|---|---|
| EMSE | 0.3 g/L |
| Sodium sulfate | 5.0 g/L |
| Sodium dextran sulfate (molecular weight: 500,000) | 0.2 g/L |
| BSA | 2.0 g/L |
| Peroxidase | 10 kU/L |
| Cation BB | 0.14 g/L |

Second Reagent (Reagent a)

| HEPES (pH 7.0) | 10 mmol/L |
|---|---|
| 4-AA | 0.3 g/L |
| Peroxidase | 20 kU/L |
| EST "Amano" 2 | 100 kU/L |
| CHO-PEL | 1.2 kU/L |

Example 5

Using the kit of Example 1, HDL cholesterol in each of 40 specimens of human serum was measured with Hitachi 7170S autoanalyzer.

(1) Preparation of Calibration Curve

Employing Hitachi 7170S autoanalyzer, a calibration curve showing the relationship between HDL cholesterol concentration and "absorbance" was prepared using a physiological saline (HDL cholesterol concentration: 0.0 mg/dL) and a serum (HDL cholesterol concentration: 60.0 mg/dL) as standard solutions and the kit of Example 1 as a kit.

The "absorbance" here is meant to describe a value obtained by subtracting E1 from E2 based on two absorbances (E1 and E2) measured by the following reactions.

The standard solution (3 μL) and the first reagent (0.24 mL) were added to a reaction cuvette and incubated at 37° C. for 5 minutes; the absorbance (E1) of the reaction solution was measured at a main wavelength of 600 nm and a sub-wavelength of 700 nm; the second reagent (0.08 mL) was then added to this reaction solution, and was further incubated at 37° C. for 5 minutes; and the absorbance (E2) of the reaction solution was measured at a main wavelength of 600 nm and a sub-wavelength of 700 nm.

(2) Calculation of "Absorbance" for Human Serum Specimen Resulting from Reaction of Specimen with Kit of Example 1

"Absorbance" for each of the human serum specimens was measured by the same method as the "absorbance" calculation method of (1) except for using each of the specimens instead of the standard solutions in the preparation of the calibration curve in (1).

(3) Determination of HDL Cholesterol Concentration in Human Serum Specimen

The concentration of HDL cholesterol in each of the specimens was determined from the "absorbance" calculated in (2) and the calibration curve prepared in (1).

Example 6

HDL cholesterol in each of 40 specimens of human serum was measured with Hitachi 7170S autoanalyzer by the same method as in Example 5 except for using the kit of Example 2 instead of the kit of Example 1.

Example 7

HDL cholesterol in each of 40 specimens of human serum was measured with Hitachi 7170S autoanalyzer by the same method as in Example 5 except for using the kit of Example 3 instead of the kit of Example 1.

Example 8

HDL cholesterol in each of 40 specimens of human serum was measured with Hitachi 7170S autoanalyzer by the same method as in Example 5 except for using the kit of Example 4 instead of the kit of Example 1.

Comparative Example 3

HDL cholesterol in each of 40 specimens of human serum was measured with Hitachi 7170S autoanalyzer by the same method as in Example 5 except for using the kit of Comparative Example 1 instead of the kit of Example 1.

Employing the each of 40 specimens of human serum used in the measurements in Examples 5 to 8 and Comparative Example 3, HDL cholesterol in each of the specimens was measured using a method (DCM: Designated Comparison Method) as described in Clinical Chemistry, Vol. 45, No. 10, p. 1803-1812 (1999) as a reference method to compare the measurement values with those obtained in the Examples.

The correlation coefficients between measurements in each of Examples 5 to 8 and Comparative Example 3 and measurements by DCM are shown in Table 1.

TABLE 1

| Measurement Method | | Kit for Measurement | | Correlation Coefficient |
|---|---|---|---|---|
| | | First Reagent | Second Reagent | |
| Example 5 | Example 1 | Reagent A | Reagent a | 0.990 |
| Example 6 | Example 2 | Reagent B | Reagent a | 0.996 |
| Example 7 | Example 3 | Reagent C | Reagent a | 0.982 |
| Example 8 | Example 4 | Reagent D | Reagent a | 0.991 |
| Comparative Example 3 | Comparative Example 1 | Reagent E | Reagent a | 0.441 |

As apparent from Table 1, a good correlation was observed between measurements using each of the kits of Examples 1 to 4 comprising the compound (I) or the compound (II) and measurements by DCM as a reference method. On the other hand, no good correlation was observed between measurements using the kit of Comparative Example 1 comprising neither the compound (I) nor the compound (II) and measurements by DCM as a reference method.

Example 9

Employing two sera rich in LpX, an abnormal lipoprotein, obtained from patients with liver/biliary tract disease as a specimen (LpX specimen 1 and LpX specimen 2), the concentration of HDL cholesterol in each of the LpX specimens was determined with Hitachi 7170S autoanalyzer by the same method as in Example 5 using each of the kits of Examples 1 to 4 and Comparative Examples 1 and 2 as a kit for measurement. The results and the concentration of HDL cholesterol in each of the LpX specimens determined by DCM as a reference method are shown in Table 2. In Table 2, values in parentheses show the difference between the HDL cholesterol concentration of each of the LpX specimens determined by DCM as a reference method and the HDL cholesterol concentration determined by each of the methods in a case where the concentration determined by DCM is assumed as 0.

TABLE 2

| | HDL Cholesterol Concentration (mg/dL) | | | | | | |
|---|---|---|---|---|---|---|---|
| Specimen | Example 1 | Example 2 | Example 3 | Example 4 | DCM | Comparative Example 1 | Comparative Example 2 |
| LpX Specimen 1 | 2.5 (−3.1) | 5.2 (−0.4) | 4.5 (−1.1) | 5.8 (+0.2) | 5.6 (0.0) | 36.6 (+31.0) | −2.2 — |
| LpX Specimen 2 | 2.4 (−0.8) | 2.4 (−0.8) | 2.2 (−1.0) | 2.3 (−0.9) | 3.2 (0.0) | 39.1 (+35.9) | −2.8 — |

As apparent from Table 2, whereas the HDL cholesterol concentration in each of the LpX specimens determined by the method using each of the kits of Examples 1 to 4 comprising the compound (I) or the compound (II) coincide closely with the HDL cholesterol concentration in each of the LpX specimens determined by DCM as a reference method, the HDL cholesterol concentration in each of the LpX specimens determined by the method using the kit of Comparative Example 1 comprising neither the compound (I) nor the compound (II) greatly deviated from the HDL cholesterol concentration in each of the LpX specimens determined by DCM as a reference method. The HDL cholesterol concentration was determined as negative values in the method using the kit of Comparative Example 2 comprising Cation BB as a quaternary ammonium salt instead of the compound (I) and the compound (II); therefore, it proved that the HDL cholesterol concentration in each of the LpX specimens could not be accurately measured in the method using the kit of Comparative Example 2 comprising Cation BB. Thus, it proved that the use of the kit of the present invention comprising the compound (I) or the compound (II) can accurately measure HDL cholesterol in even specimens rich in LpX, abnormal specimens.

INDUSTRIAL APPLICABILITY

There are provided according to the present invention a method, a reagent and a kit for measuring HDL cholesterol in a specimen, which are useful for the diagnosis of metabolic syndromes or the like.

The invention claimed is:

1. A method for measuring cholesterol in high-density lipoprotein in a specimen, comprising
   (1) reacting the specimen with i) a cholesterol ester hydrolase and a cholesterol oxidase, or ii) a cholesterol ester hydrolase, an oxidized coenzyme, and a cholesterol dehydrogenase, in an aqueous medium comprising a polyanion, and at least one substance selected from the group consisting of a substance represented by formula (I):

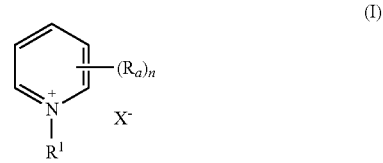

wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion, and a substance represented by formula (II):

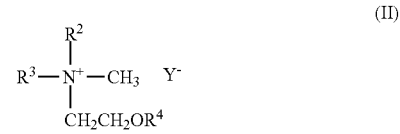

wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, substituted or unsubstituted aryl, or substituted or unsubstituted alkyl; and $Y^-$ represents a monovalent anion, to form hydrogen peroxide or a reduced coenzyme;

(2) measuring the formed hydrogen peroxide or reduced coenzyme; and
   (3) calculating the concentration of HDL cholesterol in the specimen from the value measured in (2) and a previously-prepared calibration curve showing the relationship between HDL cholesterol concentrations and measured values of hydrogen peroxide or reduced coenzyme.

2. The method according to claim 1, wherein the aqueous medium further comprises albumin.

3. The method according to claim 2, wherein the polyanion is dextran sulfate or a salt thereof.

4. The method according to claim 1, wherein the polyanion is dextran sulfate or a salt thereof.

5. A reagent for measuring cholesterol in high-density lipoprotein, comprising a polyanion, a cholesterol ester hydrolase, a cholesterol oxidase, a reagent for measuring hydrogen peroxide, and at least one substance selected from the group consisting of a substance represented by formula (I):

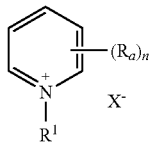

wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion, and a substance represented by formula (II):

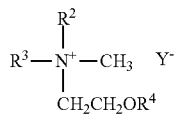

wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, a substituted or unsubstituted aryl, or a substituted or unsubstituted alkyl; and $Y^-$ represents a monovalent anion.

6. The reagent according to claim 5, further comprising albumin.

7. The reagent according to claim 6, wherein the polyanion is dextran sulfate or a salt thereof.

8. The reagent according to claim 5, wherein the polyanion is dextran sulfate or a salt thereof.

9. A reagent for measuring cholesterol in high-density lipoprotein, comprising a polyanion, a cholesterol ester hydrolase, a cholesterol dehydrogenase, an oxidized coenzyme, and at least one substance selected from the group consisting of a substance represented by formula (I):

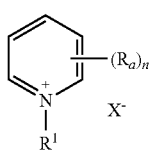

wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion, and a substance represented by formula (II):

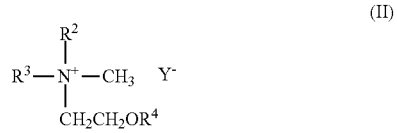

wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, a substituted or unsubstituted aryl, or a substituted or unsubstituted alkyl; and $Y^-$ represents a monovalent anion.

10. The reagent according to claim 9, further comprising a reagent for measuring a reduced coenzyme.

11. The reagent according to claim 9, further comprising albumin.

12. The reagent according to claim 11, wherein the polyanion is dextran sulfate or a salt thereof.

13. The reagent according to claim 9, wherein the polyanion is dextran sulfate or a salt thereof.

14. The reagent according to claim 10, further comprising albumin.

15. The reagent according to claim 14, wherein the polyanion is dextran sulfate or a salt thereof.

16. The reagent according to claim 10, wherein the polyanion is dextran sulfate or a salt thereof.

17. A kit for measuring cholesterol in high-density lipoprotein comprising a first reagent and a second reagent, wherein a polyanion, and at least one substance selected from the group consisting of a substance represented by formula (I):

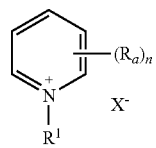

wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion, and a substance represented by formula (II):

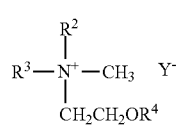

wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, a substituted or unsubstituted aryl, or a substituted or unsubstituted alkyl; and $Y^-$ represents a monovalent anion are comprised in the first reagent, a cholesterol oxidase is comprised in the second reagent, a reagent for measuring hydrogen peroxide is comprised in either the first or second reagent, or in both of the first and second reagents, and a cholesterol ester hydrolase is comprised in either the first or second reagent, or in both of the first and second reagents.

18. The kit according to claim 17, further comprising albumin in either the first or second reagent, or in both of the first and second reagents.

19. The kit according to claim 17, wherein the polyanion is dextran sulfate or a salt thereof.

20. The kit according to claim 18, wherein the polyanion is dextran sulfate or a salt thereof.

21. A kit for measuring cholesterol in high-density lipoprotein comprising a first reagent and a second reagent, wherein a polyanion, and at least one substance selected from the group consisting of a substance represented by formula (I):

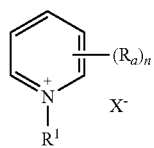

(I)

wherein $R^1$ represents a substituted or unsubstituted alkyl or alkenyl having 8 to 14 carbon atoms; $R_a$ represents a hydrogen atom, a substituted or unsubstituted alkyl, or a substituted or unsubstituted alkenyl; n represents an integer of 1 to 5; and $X^-$ represents a monovalent anion, and a substance represented by formula (II):

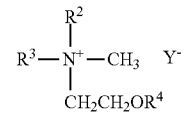

(II)

wherein $R^2$ represents a substituted or unsubstituted alkyl or alkenyl having 6 to 30 carbon atoms; $R^3$ represents a substituted or unsubstituted alkyl having 1 to 6 carbon atoms or alkenyl having 2 to 6 carbon atoms; $R^4$ represents a hydrogen atom, a substituted or unsubstituted aryl, or a substituted or unsubstituted alkyl; and $Y^-$ represents a monovalent anion are comprised in the first reagent, a cholesterol dehydrogenase is comprised in the second reagent, an oxidized coenzyme is comprised in either the first or second reagent, or in both of the first and second reagents, and a cholesterol ester hydrolase is comprised in either the first or second reagent, or in both of the first and second reagents.

22. The kit according to claim 21, further comprising a reagent for measuring a reduced coenzyme in either the first or second reagent, or in both of the first and second reagents.

23. The kit according to claim 21, further comprising albumin in either the first or second reagent, or in both of the first and second reagents.

24. The kit according to claim 23, wherein the polyanion is dextran sulfate or a salt thereof.

25. The kit according to claim 22, further comprising albumin in either the first or second reagent, or in both of the first and second reagents.

26. The kit according to claim 25, wherein the polyanion is dextran sulfate or a salt thereof.

27. The kit according to claim 21, wherein the polyanion is dextran sulfate or a salt thereof.

28. The kit according to claim 22, wherein the polyanion is dextran sulfate or a salt thereof.

* * * * *